(12) United States Patent
Tse

(10) Patent No.: US 6,670,814 B2
(45) Date of Patent: Dec. 30, 2003

(54) SEMI-INSULATING MATERIAL TESTING AND OPTIMIZATION

(75) Inventor: Ming-Kai Tse, Lexington, MA (US)

(73) Assignee: Quality Engineering Associates, Inc., Burlington, MA (US)

( * ) Notice: Subject to any disclaimer, the term of this patent is extended or adjusted under 35 U.S.C. 154(b) by 0 days.

(21) Appl. No.: 10/121,436

(22) Filed: Apr. 12, 2002

(65) Prior Publication Data

US 2002/0196028 A1 Dec. 26, 2002

Related U.S. Application Data (63) Continuation of application No. PCT/US00/28644, filed on Oct. 16, 2000.
(60) Provisional application No. 60/192,203, filed on Mar. 27, 2000, and provisional application No. 60/159,857, filed on Oct. 15, 1999.

(51) Int. Cl.$^7$ ............................................. G01N 27/60
(52) U.S. Cl. ........................................................ 324/455
(58) Field of Search ................................. 324/455, 452, 324/457, 663, 693; 399/31, 32, 27, 28, 170, 159; 250/324, 325, 326; 430/58.05, 57.1; 428/323

(56) References Cited

U.S. PATENT DOCUMENTS

| | | | | |
|---|---|---|---|---|
| 3,406,334 A | * | 10/1968 | Marquert et al. | 324/455 |
| 4,800,337 A | * | 1/1989 | Cox et al. | 324/455 |
| 5,498,974 A | * | 3/1996 | Verkuil et al. | 324/767 |
| 5,629,920 A | * | 5/1997 | Sakano et al. | 369/120 |
| 5,732,311 A | * | 3/1998 | May et al. | 399/159 |
| 5,848,322 A | * | 12/1998 | Chen et al. | 399/57 |

* cited by examiner

*Primary Examiner*—Anjan K. Deb
(74) *Attorney, Agent, or Firm*—Weingarten, Schurgin, Gagnebin & Lebovici LLP

(57) ABSTRACT

A test system and data analysis procedure are provided for use in electrophotographic printing with a whole set of characteristics determined to be important for efficiency and high quality images. The test system and data analysis procedure characterize dielectric relaxation processes in materials in terms of charge transport parameters that may include intrinsic charge density, charge mobility, and charge injection from the contact surfaces. The materials may include photoconductive drums or belts, charging rolls, developer rolls, intermediate transfer belts and output media such as paper transparencies or textiles. The apparatus consists of a charging source, a voltage detector and a current detector in an open-circuit mode of measurement. The configuration closely simulates the actual application of the materials in electrophotography and thus, can yield information more relevant for the applications.

3 Claims, 12 Drawing Sheets

- Total Current: $J_T = [\int_o^L (\mu_p q_p + \mu_n q_n) E dx - \varepsilon (dV/dt)]/L$
- Poisson's eq.: $\partial E/\partial x = (q_p + q_n)/\varepsilon$
- Charge continuity: $\partial q/\partial t = - \partial (\mu q E)/\partial x$
- Field-dep. Mobility: $\mu(E) = \mu_o (E/E_o)^p$
- Injection currents:
  $J_{inj}(O) = s E(O)$
- ✓ Roles of $\mu$ and q treated separately, not as a product $\mu q = \sigma = 1/\rho$

- Total Current: $J_T = [\int_0^L (\mu_p q_p + \mu_n q_n) E dx - \varepsilon (dV/dt)]/L$
- Poisson's eq.: $\partial E/\partial x = (q_p + q_n)/\varepsilon$
- Charge continuity: $\partial q/\partial t = -\partial(\mu q E)/\partial x$
- Field-dep. Mobility: $\mu(E) = \mu_o (E/E_o)^p$
- Injection currents:
  $J_{inj}(O) = s E(O)$
- ✓ Roles of $\mu$ and $q$ treated separately, not as a product $\mu q = \sigma = 1/\rho$

- Fields in toner layer:
  $E_t(X) = E_{to} + q_t x/\varepsilon_t$
- Transfer efficiency:
  from $E_t(x_t) = 0$

$\eta = x_t/L_t = -\varepsilon_t E_{to}/q_t L_t$

- function of time, charge density $q_i$, and injection s $q_i = \sigma/(\mu_p + \mu_n)$ unit: $q_o = (\varepsilon_r V_b/L_r^2)$ $\approx 3 \times 10^{-6}$ C/cm$^3$

- Sensitive to injection (s) at low $q_i$

- Process time:
  $t_{proc} > t_F = m(L_r^2/\mu_o V_b)$

- Mobility required:
  $\mu_o > m(L_r^2/t_{proc} V_b)$

$\approx m (10^{-6}$ cm$^2$/Vsec)
  for $t_{proc} = 0.1$ sec

- Total Current: $J_T = [\int_0^L (\mu_p q_p + \mu_n q_n)E dx - \varepsilon (dV/dt)]/L$
- Poisson's eq.: $\partial E/\partial x = (q_p + q_n)/\varepsilon$
- Charge continuity: $\partial q/\partial t = -\partial(\mu qE)/\partial x$
- Field-dep. Mobility: $\mu(E) = \mu_0 (E/E_0)^p$
- ✓ Injection currents:
  $J_{inj}(O) = s_0 E(O)$;   $J_{inj}(L) = s_1 E(L)$
- ✓ Separate independant roles of $q$ and $\mu$, not as $\sigma = \mu q$
- Increased by corona
- Decreased by:
  *Depletion of intrinsic charge $q_i$
  * Transit of injected charge
- Intrinsic $q_i$ varied
- Long $t_{chg} \gg 10 t_o$
  $V_s$ indep. of $q_i$
- Short $t_{chg} < 10 t_o$
  low $V_s$ for high $q_i$

*FIG. 12*

V in corona cut-off $V_{mx}$.
time in $t_o = L^2/\mu V_{mx}$
$q_i$ in $q_o = \varepsilon V_{mx}/L^2$

*FIG. 13*

- Dependence on Injection ($s_1$) for $0.01 < s < 0.1$

Charge: $\Delta V \simeq 0.07$

*FIG. 14a*

Discharge: $\Delta V \simeq 0.4$

*FIG. 14b*

- Intrinsic charge density (larger) $q_i = q_o$
- Lower $V_{chg}$, weaker depend. on $s_1$ (0.01<$s_1$<1)
- $V_{dischg}$: Strong dependence on $s_1$

FIG. 15

- Steady state current $J_{ss}$ determined by charge injection s, independent of intrinsic charge density $q_i$
- Time to reach steady state increases with $q_i$ → estimates of $q_i$

FIG. 16

- For high charge injection, $J_{ss} < J_o = \varepsilon\mu V_{mx}^2/L^3 \approx J_{SCL}$ or < $J_{mx}$ whichever is less
- Mobility $\mu > \sim J_{ss} L^3/\varepsilon V_{mx}^2$

- Time Integral of Charging Current with injection-blocked sample
- $Q_c = [V_{mx} + Q_i L_s / \varepsilon_s]/(L_1/\varepsilon_1 + L_2/\varepsilon_2 + L_s/\varepsilon_s)$ for $Q_i = q_i L_s <\!\!- V_{mx}/(L_1/\varepsilon_1 + L_2/\varepsilon_2)$ $Q_{cmx} = V_{mx}/(L_1/\varepsilon_1 + L_2/\varepsilon_2)$

FIG. 21

- Effective R and $\sigma$: $R_e = L/\sigma_e A$
- $J_{ss} = J_{mx}(R_b/R_e) = J_{mx}/(1 + R_e/R_{ch})$

$= J_{mx}/(1 + L/\sigma_e AR_{ch})$ (red curve)

$\rightarrow \sigma_e = J_{ss} L/AR_{ch}(J_{mx} - J_{ss})$

- Expt'l data (HV= 6kV):

$J_{mx} = 11.5\mu A$; $L = 10^{-2}$ cm $R_{ch} = 0.805 \times 10^8 \Omega$; $A = 1$ cm$^2$

|  | 2-blck | 1-blck | No-blck |
|---|---|---|---|
| obs. $J_{ss}/J_{mx}$ | 0.05 | 0.086 | 0.31 |
| calc. $\sigma_e$ | 0.065 | 0.12 | 0.55 ($10^{-10}$S/cm) |
| calc. $R_e$ | 15.4 | 8.3 | 1.82 ($10^8 \Omega$) |

(agree with results from $V_{ss}/J_{ss}$)

$\sigma_e$ of the same sample varies due to different injection

FIG. 22

- Scanning Charger and Probe
  Speed=s; Size=$W_c$ and $W_p$
  Separation (tail-to-head)= $d_{cp}$
  - Charging time: $t_c = W_c/s$

- Voltage decay after charging:
  $V(t') = V(t_c)\exp(-t'/R_e C)$, $(t' = t - t_c)$

- Measured Voltage: $V_{av}$ (average over $W_p$)
  $x = x_0$ to $x_0 - W_p$ ; or $t' = t_s$ to $t_s + t_p$ where $t_s = d_{cp}/s$, $t_p = W_p/s$
  $V_{av} = V(t_c)(R_e C/t_p)\exp(-t_s/R_e C)[1 - \exp(-t_p/R_e C)]$

- Measured Current: $J_{av}$ (average over $W_c$)
  $x = x_0$ to $x_0 + W_c$, or $t = t_c$ to 0
  $J_{av} = J_{mx}(R_b/R_e)\{1 + (CR_e R_b/t_c R_{ch})[1 - \exp(-t_c/CR_b)]\}$

- Apparent resistance defined as,
  $R_a = V_{av}/J_{av}$

FIG. 23

- Scanning Charger and Probe
- Measured Voltage: $V_{av}$, average over $W_p$
  $x = x_0$ to $x_0 - W_p$ ; or $t = t_s$ to $t_s + t_p$

- Measured Current: $J_{av}$, average over $W_c$
  $x = x_0$ to $x_0 + W_c$ ; or $t = t_c$ to 0

- Apparent Resistance
  $R_a = V_{av}/J_{av}$
  varies with scan
  speed s, equivalent $R_e$,
  probe/charger size,
  $t_p/t_c$ probe-charger
  separation charger
  J-V characteristics

FIG. 24

- Air gap Voltage vs. Paschen curves

*FIG. 25*

- Air gap Voltage vs. Paschen curves

*FIG. 26*

- Cause: Images on back side block charge injection
- Sensitivity of Transfer Efficiency to injection (s) at various process times
- Slope represents sensitivity
- Smaller for larger intrinsic charge density density $q_i$ → less print-through

*FIG. 27*

- Cause: Images on back side block charge injection
- Sensitivity of Transfer Efficiency to injection (s) at various process times
- Slope represents sensitivity
- Smaller for larger intrinsic charge density density $q_i$ → less print-through

*FIG. 28*

- Transfer Efficiency vs. Injection (s) for various $q_i$
- Long process time: $t > \sim 10$
  - full transfer at any $q_i$ for $s > \sim 0.1$
  - as $q_i$ decreases, required s and sensitivity to s increases → mores print-through

*FIG. 29*

- Transfer Efficiency vs. Injection (s) for various $q_i$
- Long process time: $t > \sim 10$
  - full transfer at any $q_i$ for $s > \sim 0.1$
  - as $q_i$ decreases, required s and sensitivity to s increases → mores print-through

- Transfer Efficiency vs. Injection (s) for various $q_i$
- at short process time: $t \approx 1$
  - weak sensitivity (slope)
  - efficiency < 1 for small $q_i$

FIG. 32

- Good transfer (B01) - Slow ECD decay
  Poor transfer (B02) - Fast ECD decay
- RSC of B02 more conductive than B01 (from ECD)
- ES transfer with positive bias $V_b$
- Negative charge induced in RSC through leakage path shields bias voltage
- Poor transfer for more conductive RSC (B02)

FIG. 33

- Transfer of second color limited by charges in toners and receiver from first color transfer
- Neutralization of toner charge and receiver charge
- Current: $J_n = -dQ_{rt}/dt = Q_{rt}/t_n$
  $Q_{rt}$ = interface charge density; $t_n$ = time const

SEMI-INSULATING MATERIAL TESTING AND OPTIMIZATION

This is a continuation of International Application No. PCT/US00/28644 with an international filing date of Oct. 16, 2000.

CROSS REFERENCE TO RELATED APPLICATION

This application claims priority of U.S. Provisional Patent Application No. 60/159,857 Entitled: SEMI-INSULATING MATERIAL TESTING AND OPTIMIZATION incorporated herein by reference filed Oct. 15, 1999; U.S. Provisional Patent Application No. 60/192,203 Entitled: DIELECTRIC RELAXATION ANALYSIS SYSTEM incorporated herein by reference filed Mar. 27, 2000; and U.S. PCT International Application No. PCT/US00/12728 incorporated herein by reference filed May 10, 2000.

STATEMENT REGARDING FEDERALLY SPONSORED RESEARCH OR DEVELOPMENT

N/A

BACKGROUND OF THE INVENTION

In electrophotographic printing of images such as in the xerographic process, toner is attracted to a surface of a photoconductive drum or belt selectively charged and then transferred by electrostatic processes to print output media such as paper. The photoconductive drums or belts must function to hold a selectively applied charge corresponding to a document or image original. The output media must be able to dielectrically relax appropriately in order for fast, efficient printing of high quality images to be produced.

The properties of these materials that are so critical in the production of electrophotographic images have been poorly understood for the intended use. Traditional characterization of these materials typically involved resistance measurements and simple RC modeling, which was found to be of limited use if at all in selecting or designing materials advantageous for such uses.

Special reproduction environments present additional problems the causes of which are not well understood. These include the presence of toner scatter or print dropouts accompanying electrostatic discharge in the air gap over the paper, the potential for image deletion or image print through in duplex printing due to the presence of an image on the reverse side in the second pass through, the tendency of transparency material to not support good images printed on it and the problem of color shift due to residual charge effects in multi-pass color printing. Therefore, a novel technique for characterization of these materials for the purposes of understanding the mechanism, predicting the performance, and specification for material design, is needed.

SUMMARY OF THE INVENTION

The present invention tests materials for use in electrophotograpic printing with a whole set of characteristics determined to be important for efficiency and high quality images. The materials include, but not limited to, photoconductive drums or belts, charging rolls, developer rolls, intermediate transfer belts and output media such as paper, transparencies or textiles. It is well known that the performance of these materials in this application depends critically on the process of dielectric relaxation when the material is under electrical stress. The traditional method for electrical characterization of these materials typically involves measurements of resistance in closed-circuit experiments and analyses based on the equivalent circuit model, which have been found to be of limited success in correlating the results with the imaging performance.

In the present invention, a test system and data analysis procedure are provided to characterize dielectric relaxation process in these materials in terms of charge transport parameters that include, but not limited to, intrinsic charge density, charge mobility, and charge injection from the contact surfaces.

The apparatus of this invention consists of a charging source, a voltage detector and a current detector in an open-circuit mode of measurement. The configuration closely simulates the actual application of the materials in electrophotography and thus, can yield information more relevant for the applications (than the conventional resistance measurement in a closed circuit). Furthermore, the non-contact feature of the test system enables non-destructive, high speed scanning evaluation over a large two-dimensional area of the material. The apparatus is in part similar to the one described in commonly owned U.S. Pat. No. 5,929,640, incorporated herein by reference.

The data are processed based on a model developed from first principle charge transport theory. The model provides the procedure for deducing the above-mentioned charge transport parameters from the measured voltage and/or current. Furthermore, a single figure of merit, namely, an effective resistance or an apparent resistance, that consolidates the roles of a large number of charge transport parameters mentioned above, can also be deduced from the measured voltage and/or current for routine characterization such as in production quality control.

The data acquisition and processing described above are carried out automatically by the control software.

A good correlation has been obtained between the charge transport parameters and printing performance. Common print quality deficiencies, for example, toner scatter, image deletion, image print through in duplex printing, and color shifts in full color prints, can be attributed to inadequate dielectric relaxation in the materials involved, in this case, the transfer media. Thus, a dielectric relaxation profile of a material obtained by the technique and analysis of this invention serves the purpose of performance prediction and design guideline for new materials.

BRIEF DESCRIPTION OF THE DRAWING

These and other features of the present invention are more fully described below and in the accompanying drawing of which:

FIG. 12.

DETAILED DESCRIPTION OF THE PREFERRED EMBODIMENT

The present invention provides for a complete understanding of electrophotographic printing processes by which semi-insulating material such as media, which includes paper and the like to be printed on, or printing equipment elements like rollers, belts, and drums used in the steps of printing. In the present invention the material is characterized according to a plurality of properties affecting the efficiency of charge transport by testing in a fixed or scanning procedure. The properties include such characteristics as charge mobility, $\mu$, intrinsic charge density, q, dielectric constant, $\epsilon$, and charge injection, s. The defect detection operates in a scanning mode to identify the nature and location of a defect in the material and to characterize its resistance by apparent resistance, Ra, or effective resistance, Re.

Figure 1:
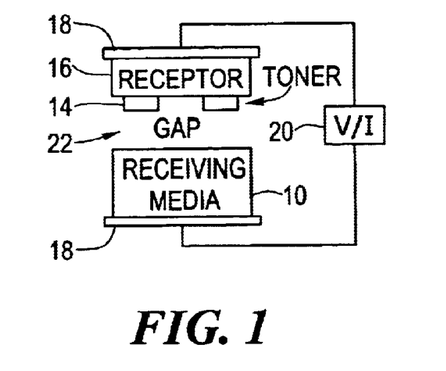
FIG. 1 is a diagram of an application of the invention.

FIG. 1 shows the application of these materials in electrophotography schematically. Exemplary of a toner transfer system includes a biased circuit 20 across the entire set of elements comprising of electrodes 18, a charged photoreceptor 16, a patterned toner layer 14, an air gap 22 and the receiver or media 10. The voltage or current applied by the biased circuit is distributed among all the elements in the circuit and generates an electric field in each element. To maximize the toner transfer efficiency, the electric field in the toner layer must be maximized. This can be accomplished effectively by relaxing (decreasing) the voltage across the media, thereby shifting the bias voltage in the media to the other elements in the circuit, including the toner layer.

Figure 2:
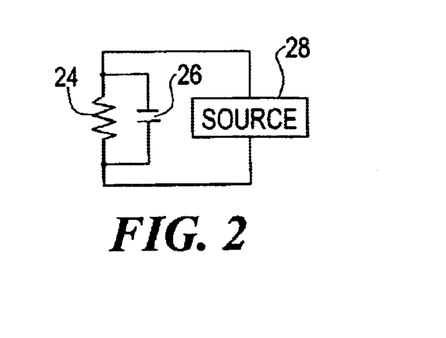
FIG. 2 is a circuit diagram of an equivalent circuit view characterizing the environment of the invention.
Figure 3:
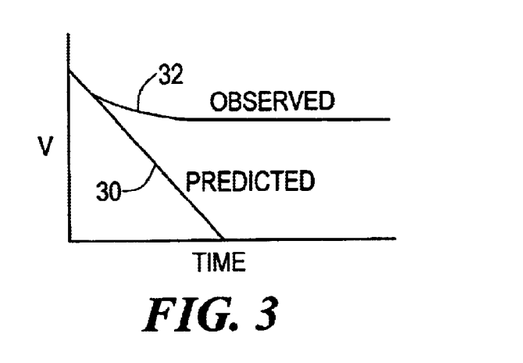
FIG. 3 is a graph illustrating the deficiency inherent in the traditional analytical model.

High efficiency which translates into fast operation and high quality printed output requires the dielectric relaxation across the media be fast and uniform. Testing of materials for this function is important to identify formulations that fit these stringent demands closely. Traditional approaches have modeled the material as a RC circuit as shown in FIG. 2. There the relaxation properties are modeled as a resistance 24, capacitance 26 and conventional source of voltage 28 with the predicted relaxation 30 shown as a plot of logarithm of voltage against time in FIG. 3. Actual response of typical materials is shown in curve 32 showing how poorly the prior models have predicted material relaxation properties.

Figure 4:
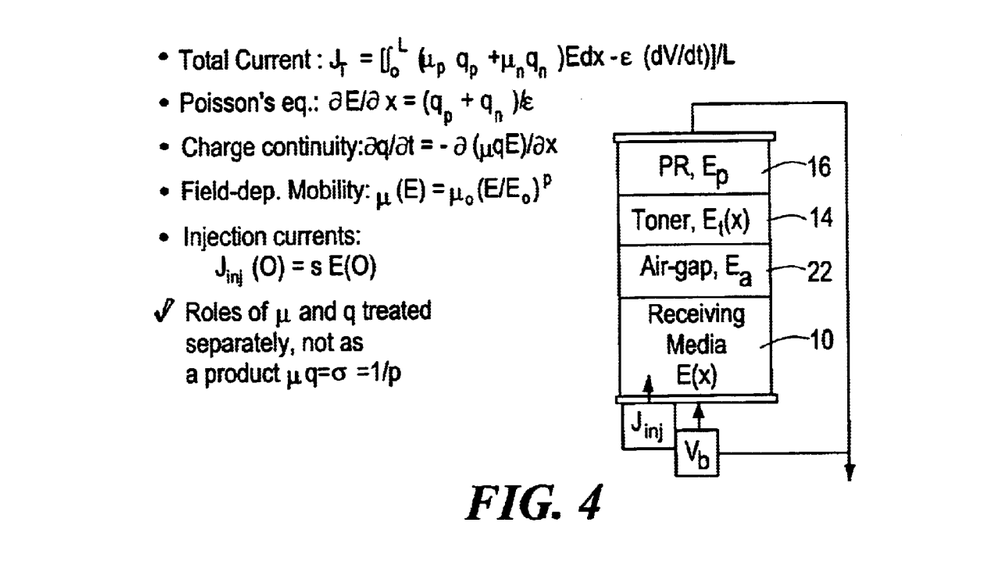
FIG. 4 is a further diagram of an application of the invention illustrating applicable theory used with the invention.

The present invention provides testing techniques that accurately determines the dielectric relaxation behavior of semi-insulating materials leading to a superior understanding of the suitability of materials and a definition of optimum properties for electrophotographic printing. FIG. 4 identifies the theoretical basis for the use of the parameters, including charge mobility, intrinsic charge density, dielectric constant and charge injection, in describing such dielectric relaxation.

Exemplary of an application of the present invention is electrostatic toner transfer. Traditionally, conductivity of the receiving media is used as a figure of merit for transfer efficiency. The conductivity is the product of charge density and mobility. But the two factors must be treated independently, because a material of a given conductivity with a high charge density and a low mobility may not work equally as a material of the same conductivity with a low charge density and a high mobility. The mobility in materials of present interest is generally field dependent, and the dependence has important effects on the dielectric relaxation. Also, the physical condition at the interfaces between the sample and electrode can strongly influence the extent of charge injection, which in turn affects the dielectric relaxation. The extent of charge injection can be determined by steady state current measurements as described later.

Figure 5:
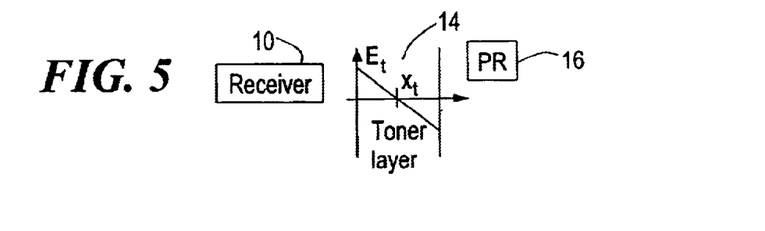
FIG. 5 illustrates the electric fields present in the environment of the application along with applicable theory.
Figure 6:
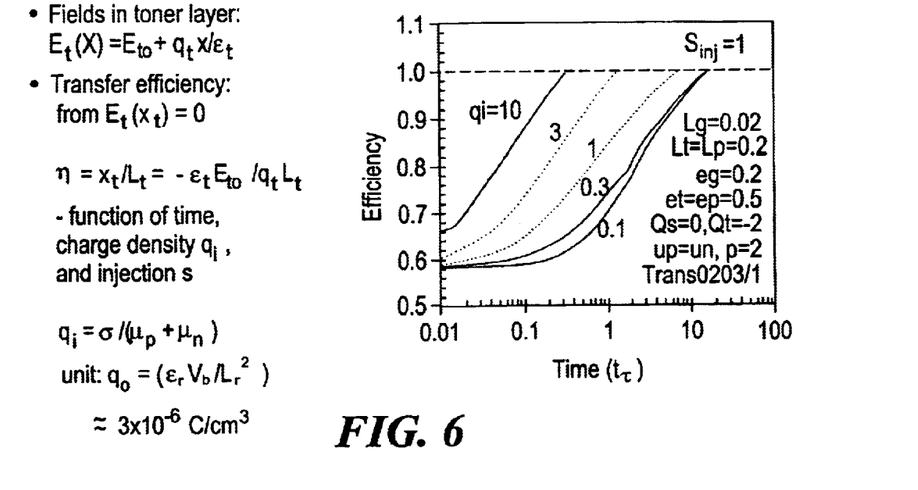
FIG. 6 is a chart and associated formulas illustrative of the effect of a parameter measured according to the invention.
Figure 7:
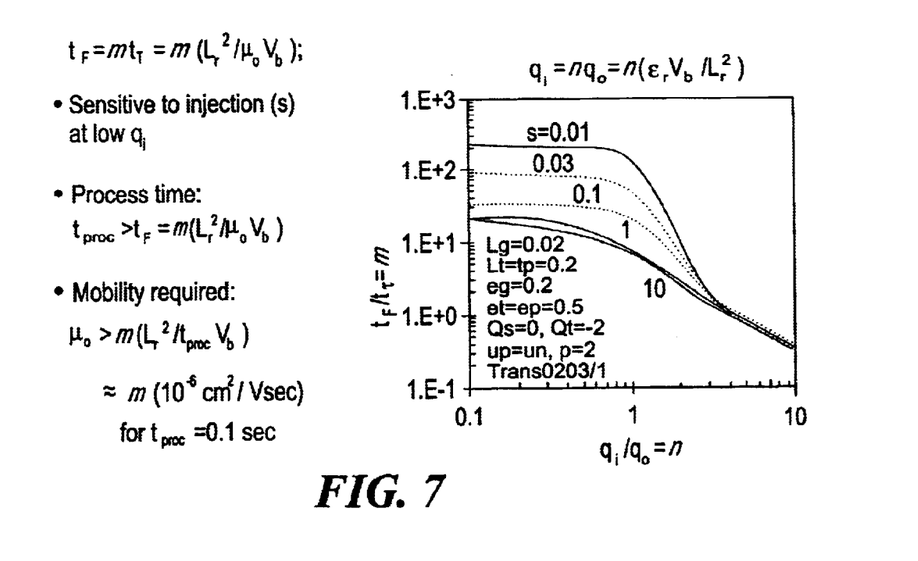
FIG. 7 is a chart and associated formulas illustrative of the effect of a further parameter measured according to the invention.

The intrinsic charge density, q, affects the efficiency of toner transfer to a receiving material as shown in FIGS. 5 and 6. FIG. 5 shows the electric field variation across the toner layer 14 at one instant of time in the transfer process. FIG. 6 shows how the efficiency increases as a function of time, where time is given in units defined in terms of transit time, tT, which is inversely proportional to mobility. The longer the time allowed for toner transfer, the larger the electric field across the air gap 22 and the toner layer 14 rather than the receiver or media 10, and hence, the greater is the efficiency or amount of toner to be transferred. The nested curves show that the efficiency increases dramatically with increasing intrinsic charge density of the material. For smaller q, the efficiency is further dependent on charge injection, s. As shown in FIG. 7, the time for full transfer, tf, increases as charge injection decreases. In practice, because the process time in a given printer has to be longer than the time to full transfer, a lower limit on mobility in the receiver can be derived from the time to full transfer, process time, the receiver layer thickness, and the bias voltage.

Figure 8:
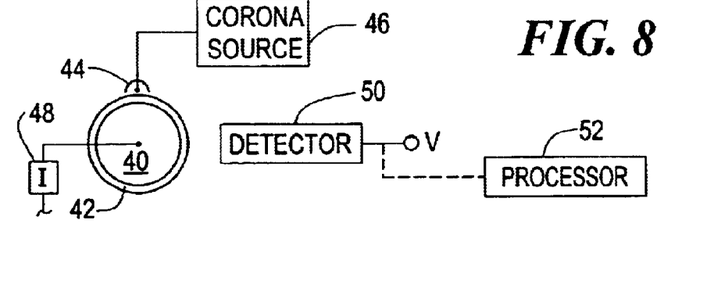
FIG. 8 is a diagram of apparatus useful in performing measurements according to the invention.

Apparatus for the measurement of these and other parameters that predict the dielectric relaxation and resulting efficiency of materials and media for the creation of images by electrophotography is shown in FIGS. 8–11. FIG. 8 shows a rotating drum 40 having a material 42 such as a coating or paper sheet, to be tested for dielectric relaxation firmly placed around it. A corona charge applicator 44, energized by a source 46, charges the material 42. The drum 40 conducts, through current sensor 48, to facilitate the relaxation of the material 42. The voltage on the material is sensed by a non-contact detector 50 placed at a distance from the corona charger 44. The voltage output is measured as a function of time since the application of the charge. This signal, along with outputs from other units descried below, is used in a processor 52. The current output during corona charging is sensed by a current sensor 48 connected to the rotating drum 40. The apparatus of FIG. 8 is more fully described in part in commonly owned U.S. Pat. No. 5,929,640, incorporated herein by reference.

Figure 9:
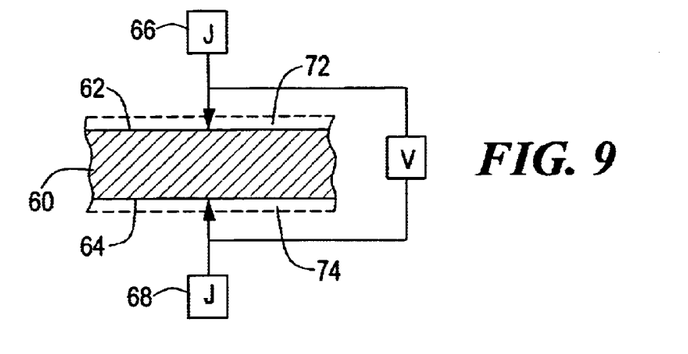
FIG. 9 illustrates a further form of apparatus for performing measurements according to the invention.

FIG. 9 shows further apparatus used for determining responses of a material to the application of a current and that is used in determining the dielectric relaxation parameters such as charge injection. A body of material 60 is instrumented to receive current on either or both the top and bottom surfaces 62 and 64 from current sources 66 and 68 which can include a corona source. A voltage sensor 70 detects the surface voltage over time resulting from the application of a current to either or both of the surfaces 62, 64. Insulating (or, blocking) layers 72 and/or 74 are added selectively to isolate one or both surfaces to enable detection of injection properties for each surface.

Figure 10:
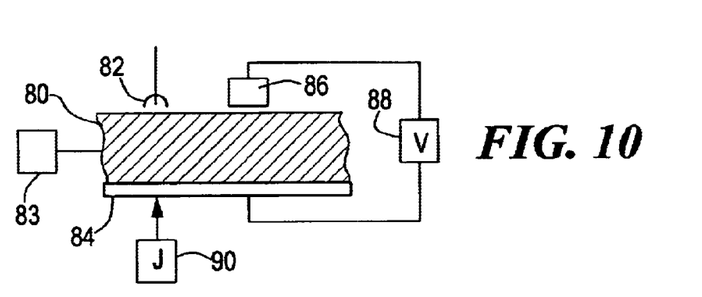
FIG. 10 illustrates an alternative form of scanning apparatus for performing measurements according to the invention.

FIG. 10 shows a test set-up similar to that of FIG. 8 except that a combination 83 of a corona source 82 and a voltage sensor 86 moves along the axial direction of a cylindrically shaped sample or helically around the sample. Corona source 82 applies a charge and the resulting voltage is sensed by a non-contact sensor 86 and processed by voltage processor 88. Such a processor may be used with all the other tests described for calculation and other purposes. A current sensing circuit 90 is provided for detecting the current from the material in response to the application of a voltage or current.

Figure 11:
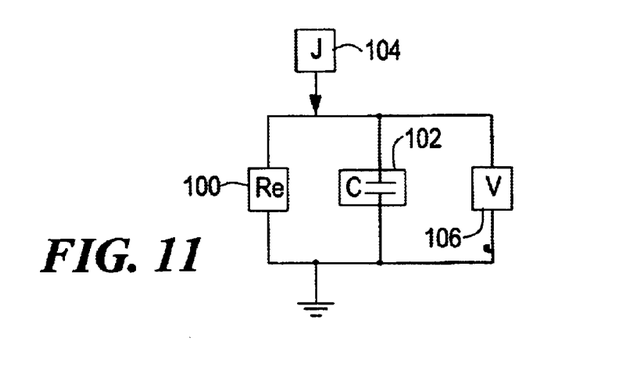
FIG. 11 illustrates an equivalent circuit formulation for expressing parameters according to the invention.

FIG. 11 shows an equivalent circuit for the replacement of the resistance R of a conventional model for the dielectric relaxation of a material with a parameter, Re 100, that is determined from the testing with the apparatus shown above and described below.

Figures 12, 13, 14A, 14B:
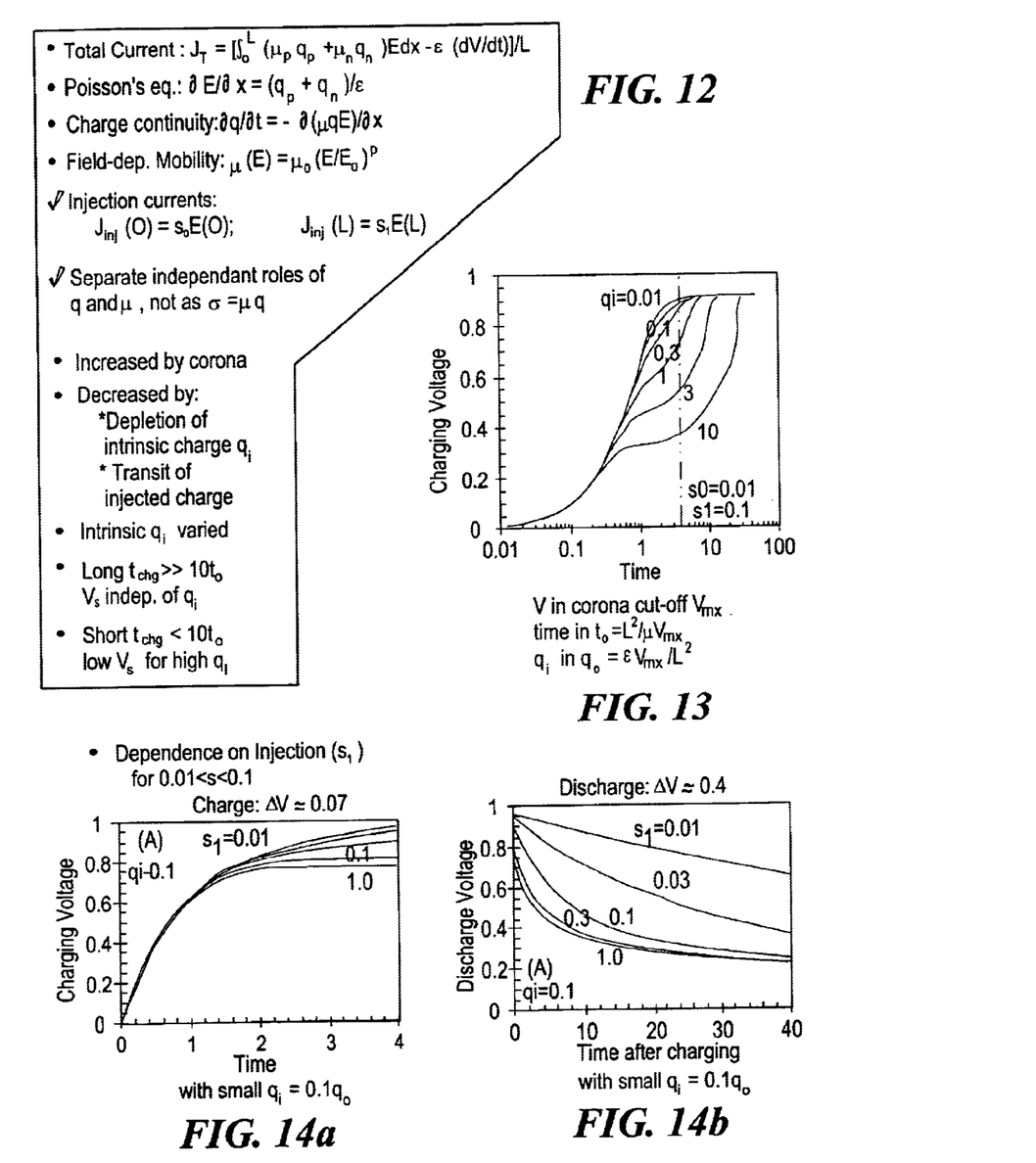
FIG. 12 shows theoretical relations.
FIG. 13 is a graph illustrating the effect of a material parameter on charging voltage over time.
FIGS. 14a and 14b are graphs illustrating the effects on charging and discharging situations of a parameter measured according to the invention.

Using apparatus above, such as that in FIG. 8 or 10, a charge is applied to a test material and the buildup of the charge measured as voltage or current as a function of time at a controlled scanning speed. FIG. 12 shows the theoretical relations between the above parameters in material 100 and the measured voltage or current. Typical results are shown in FIGS. 13–16. In FIG. 13, the curves show the effect of intrinsic charge density on the build up of the voltage. The larger the charge density, the slower is the build up.

Figure 15:
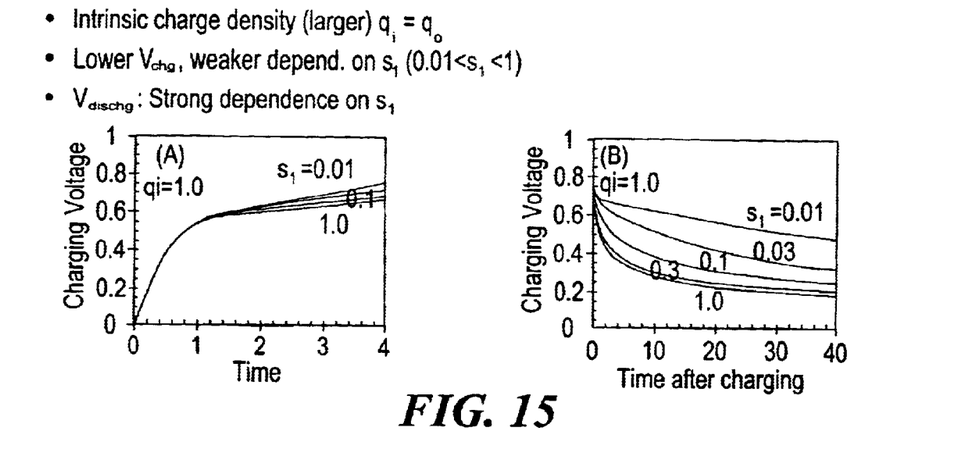
FIG. 15 is a graph illustrating the effects on charging and discharging situations of a parameter measured according to the invention.

FIGS. 14a and 14b show the effects of charge injection, specified by the parameter "s", on the buildup and the decay of the voltage respectively. It is shown that the build-up is less sensitive than the decay to variation in charge injection. The same effect is seen in FIG. 15, in which the material has an order of magnitude higher charge density than that in FIG. 14. Additionally, it can be seen that the higher charge density reduces the charging voltage than that in FIG. 14.

The above and related experimental results lead to a set of criteria for designing receiver materials such as intermediate transfer belt, transfer rollers or paper for efficient transfer. High charge density is essential for good transfer efficiency. In the case of transfer belt or rollers, however, the stability of charge injection becomes equally critical since the surface conditions of the receiver material may degrade over time in use.

Using the apparatus of FIG. 9, the injection parameter, "s" can be found for both the top and bottom surfaces of the material. This is done by applying a current to the material with no blocking layer and with one blocking layer on each side. The steady state current with no blocking layers is a combination of the surface charge injection of both surfaces. These are separated using a blocking layer for each surface separately and a corona application of voltage. The current will fall off as a function of time to some steady state level as the material collects charge. These will differ, or not, as a function of the surface being not blocked.

Figure 16:
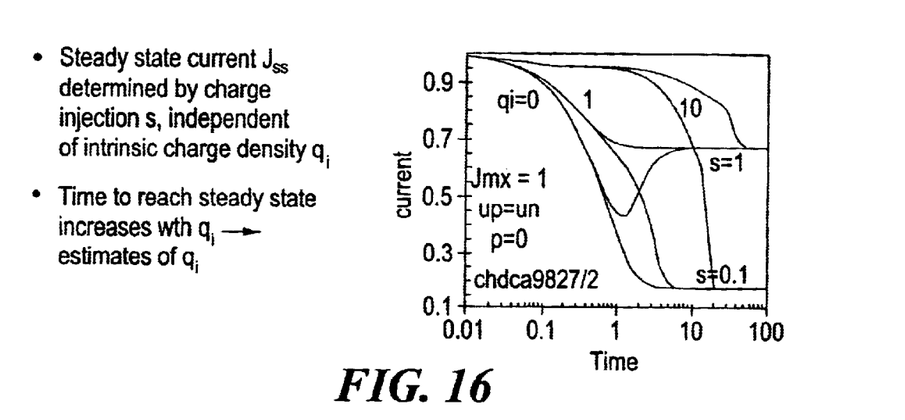
FIG. 16 is a graph illustrating the effect on relaxation current of two parameters measured according to the invention.

FIG. 16 shows the effect of charge injection on the steady state current, and suggests the use of steady state current for the determination of charge injection level. These are in normalized values which can be resolved to real numbers by those skilled in the art.

Charge mobility is determined from experimental results of steady current measurements utilizing the physics that relates the charging current into a material, its dimensions and the voltage across the material. This relationship can be expressed as:

$$J_{ss} < J_o = \epsilon\mu V_{max}^2/L^3.$$

Figure 17:
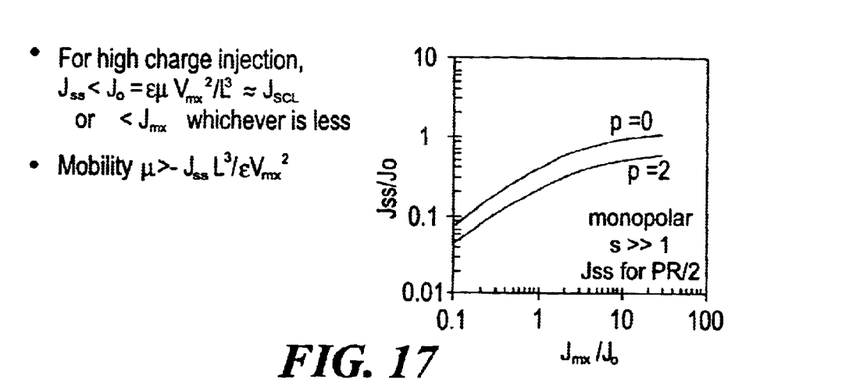
FIGS. 17–19 are graphs and associated formulas illustrating techniques for determining a further parameter according to the invention.
Figure 18:
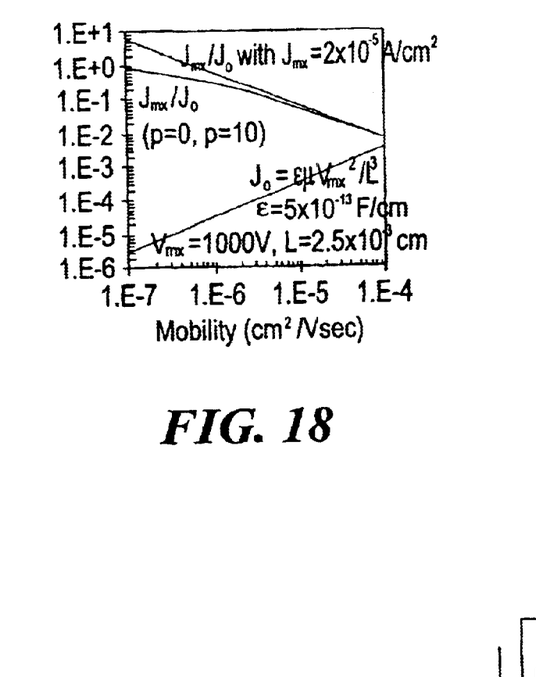
Figure 19:
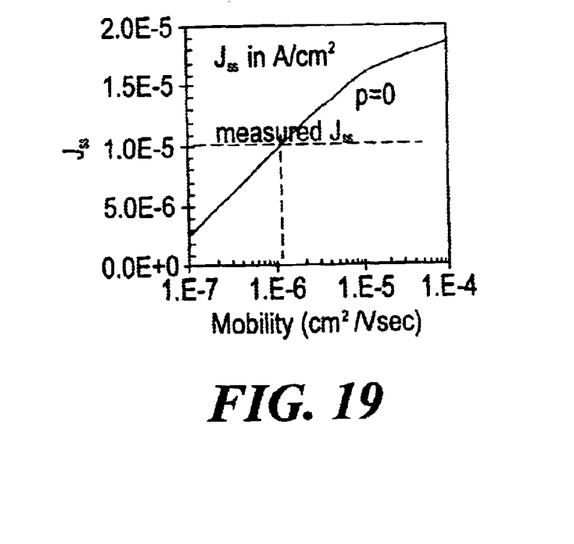

This relationship places a lower bound on the mobility. The Jss or steady state current, measured from the techniques above should be less than the space-charge-limited current, Jo, and less than Jmax as shown in FIG. 17. The maximum charging or cut-off voltage (Vmax) of the corona and thickness, L, of the material are design parameters known in advance. The dielectric constant is determined by conventional methods for the material. Using an iterative procedure as shown in FIGS. 18 and 19 involving normalized values of Jmax/Jo and Jss/Jo, it is possible to obtain the lower bound value of the mobility. Mobility is typically a function of the polarity of the charging current and must be done with both positive and negative corona sources to get the values for both.

Figure 20:
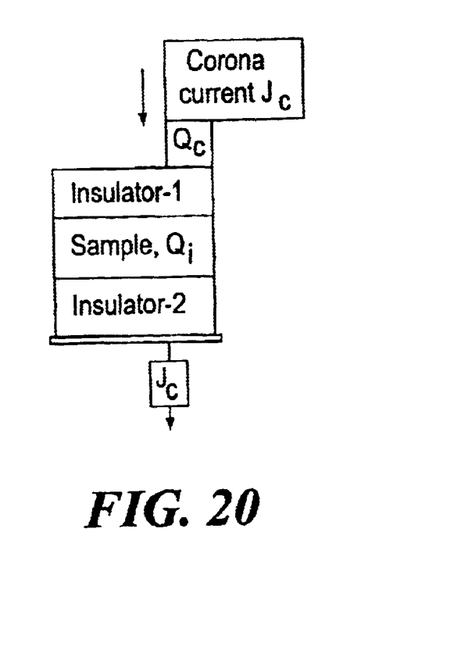
FIG. 20 is a diagram of a measurement set up useful in the invention.

Charge density is determined using a set up of the type shown in FIG. 9 using a corona for source 66 and with both blocking layers 72 and 74 in place, schematically shown in FIG. 20. The intrinsic charge density is determined by the integral of the charging current, per unit of material, from its initial high value at the time of activation of the corona to zero when the corona cut off occurs.

Figure 21:
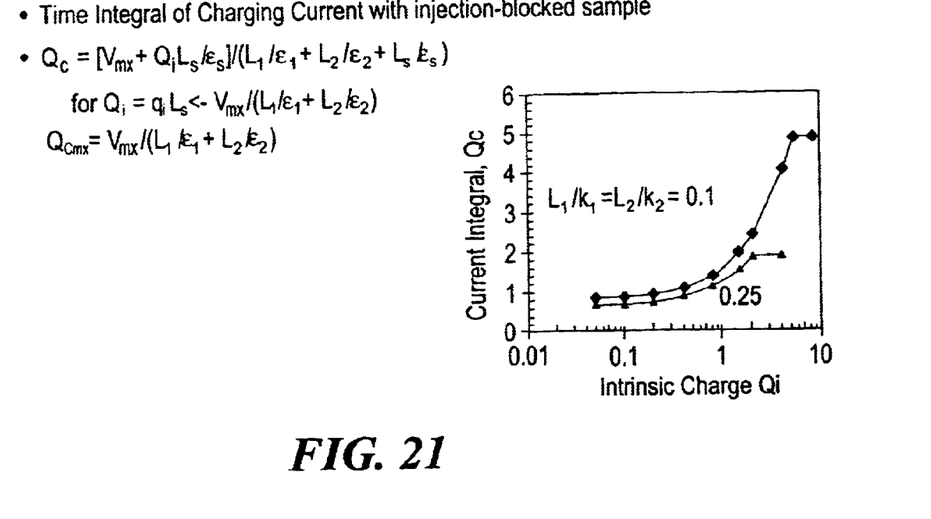
FIG. 21 is a graph and associated formulas useful in determining a parameter of dielectric relaxation according to the invention.

The apparatus will, in its data, include the effect of the blocking layers and this must be factored out in the final figures for intrinsic charge density using the equations associated with FIG. 21. The subscripts 1, 2 and s represent the first and second insulator dimensions of length, L, and k dielectric constant, with Vmx being the corona cut-off voltage.

The totality of these parameters present a level of complexity necessary to fully understand the characteristics of a material either as a transport material or print media. They are not as convenient in all cases as a single R and so there is a value to return to the simple model of an RC circuit shown in FIG. 11 to come up with an effective resistance, Re, to describe the material's bulk resistance and its surface charge injection properties. Such an effective resistance, which can be used as a figure of merit for quality control, comparison or advertising purposes, can be arrived at using the information provided below.

Figure 22:
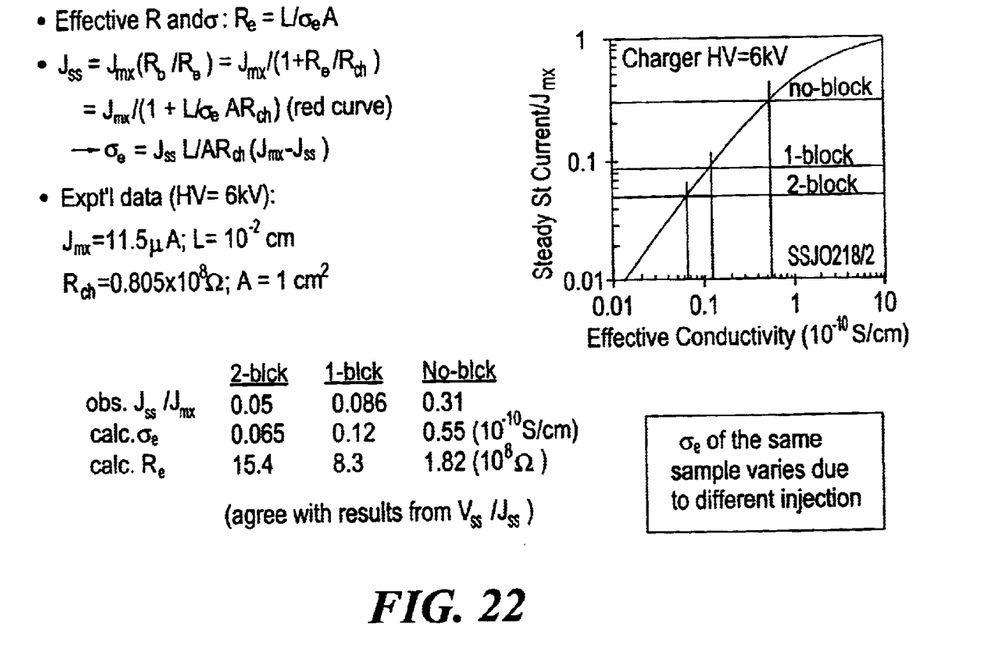
FIG. 22 is a graph and associated formulas illustrating the relationship between a parameter measured according to the invention and other electrical properties.

FIG. 22 illustrates the variation of effective conductivity, and its mathematically related resistivity, in actual experimental measurements and calculations. Here, $R_{ch}$ is the ratio of $V_{max}/J_{max}$ as defined above and $R_b = R_e R_{ch}/(R_e + R_{ch})$.

The effective resistance can be shown to be equal to the ratio of the voltage to the current values at steady state in the measurements using FIG. 9 apparatus with full or partial blocking. This effective resistance is solely determined by charge injection and is independent of intrinsic charge density.

Figure 23:
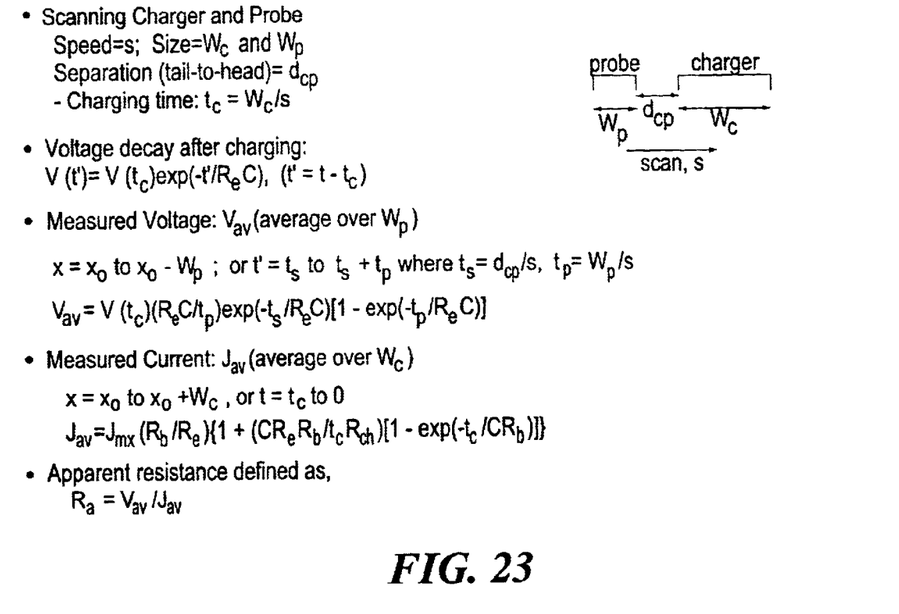
FIG. 23 is a diagram of portions of measurement apparatus and associated formulas useful in describing a measurement technique and associated calculation of a parameter according to the invention.
Figure 24:
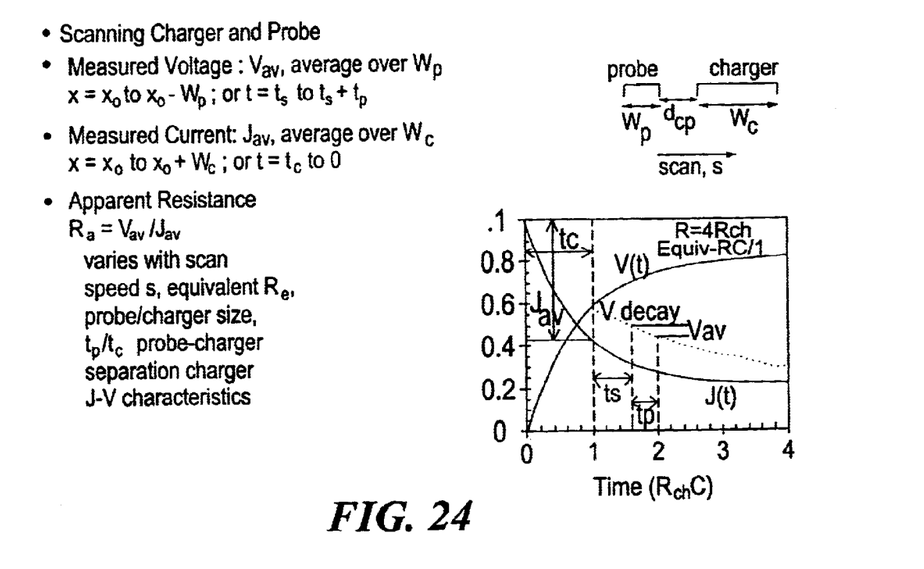
FIG. 24 is a graph illustrating the interdependence of the dimensions in the apparatus of FIG. 23 and measured parameters.

In cases where scanning apparatus of the sort illustrated in FIG. 8 or 10 are used, the time delay between charge application at the corona source and the point of detection, illustrated schematically in FIG. 23 has an effect on the measurement of the resistance. To account for this effect, an apparent resistance, defined as $Ra = V_{av}/J_{av}$ in FIG. 24, is obtained from experiments. Based on the theory described in FIG. 23, the effective resistance Re can be deduced from the value of Ra.

Figure 25:
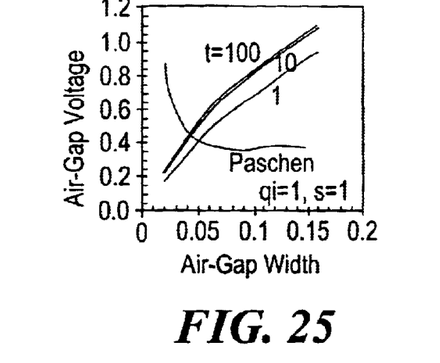
FIGS. 25 and 26 are graphs illustrating the considerations in selecting materials according to the invention for use in applications involving air breakdown.
Figure 26:
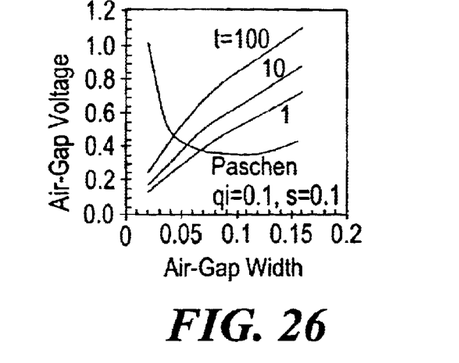
Figure 27:
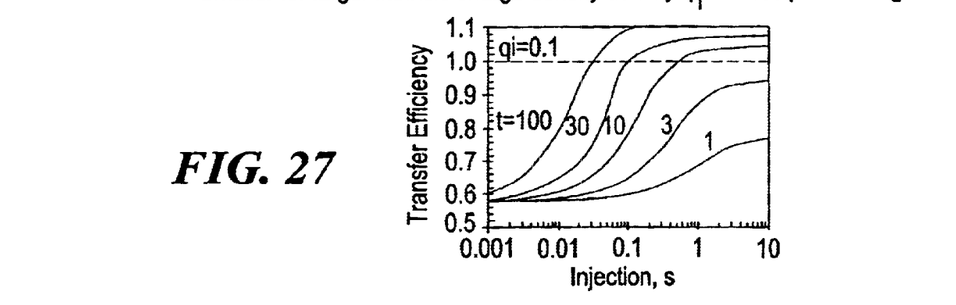
FIGS. 27–30 are graphs illustrating the effect on transfer efficiency of the parameters according to the invention.
Figure 28:
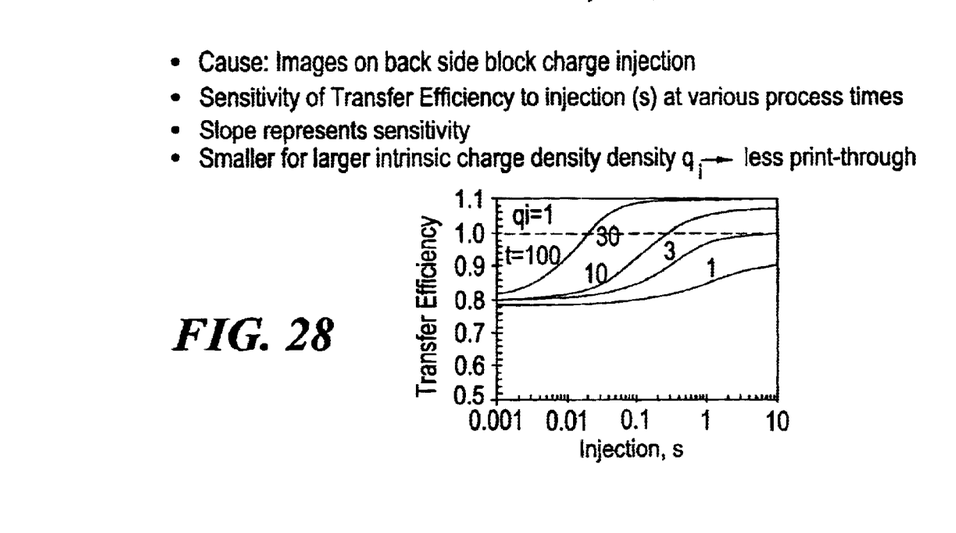
Figure 29:
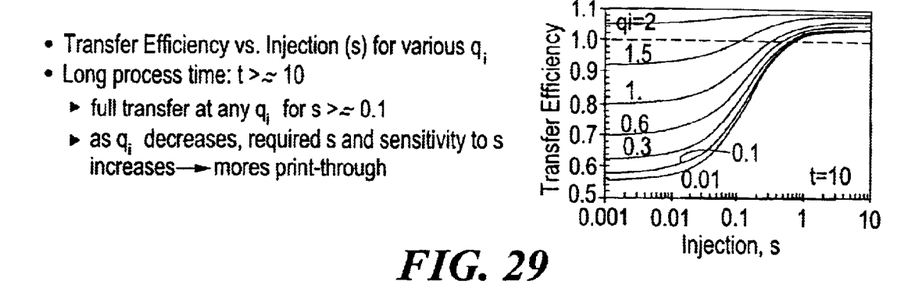
Figure 30:
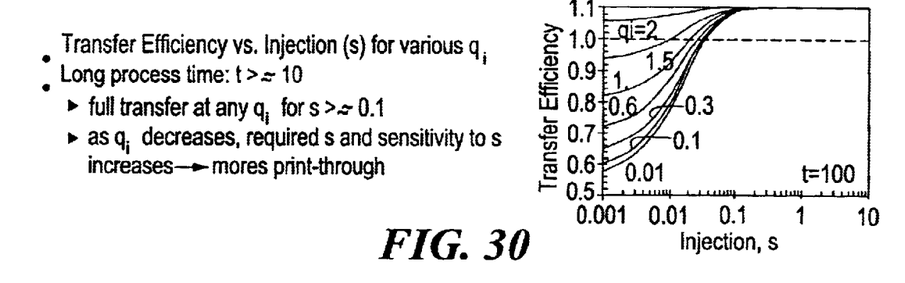

The teaching of this invention allows for the solving of various problems that affect electrophotographic printing. FIGS. 25 and 26 show the air-gap voltage as a function of air gap thickness, for process times differing by two orders of magnitude, as compared to the Paschen breakdown threshold. These are given in two sets of curves for different charge density and charge injection values. This allows a design of system and media parameters to avoid breakdown possibilities by lying outside of the Paschen threshold area. Given the fact that some safety reserve is desired and that the more irregular the paper the greater the reserve, this allows specifying those parameters more precisely.

The problem of image deletion and print through in duplex printing is addressed using the media characteristics of charge density and injection, q and s respectively, in FIGS. 27–32 as a function of time, t. The presence of image on a first side interferes with the local injection of charge and thus reduces the transfer efficiency. The figures show that with increasing q and/or s this can be reduced, in particular with q above 2 or s above 1 and t above 10, all in normalized units.

Figure 33:
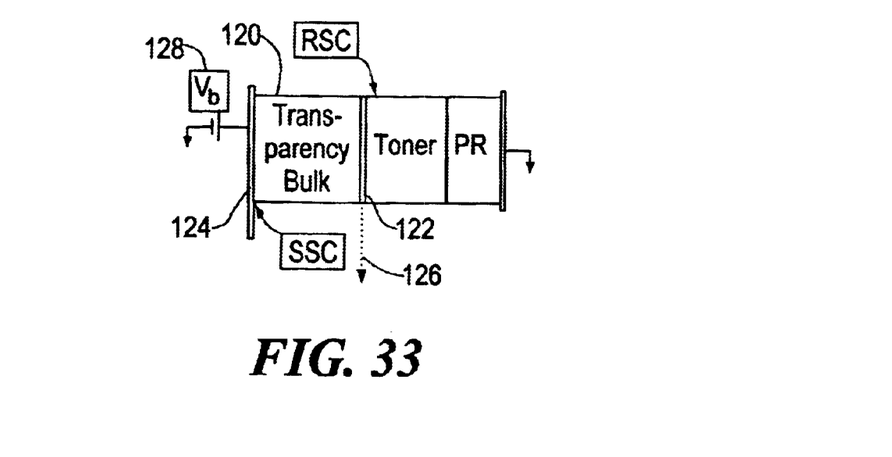
FIG. 33 is a diagram illustrating the use of the present invention with the issues involved with printing on transparency media.

In the use of transparencies for print output media, there is typically, as shown in FIG. 33, a body 120 with insulating properties preventing effective dielectric relaxation for electrophotographic printing. The substrate side and the toner receiving side are provided with more conductive anti-static coatings, SSC(124) and RSC(122), respectively. Typically a path 126 to ground exists and for more conductive layers 122 shields the effects of a positive bias 128 reducing transfer efficiency and creating poor print quality. This test procedure identifies materials with the potential to cause this residual charge and resulting poor image quality in printing.

Figure 33A:
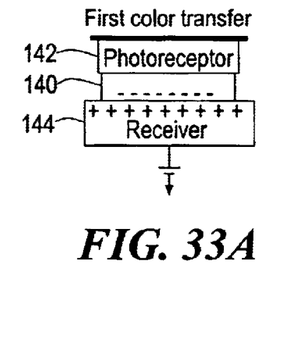
FIGS. 33a–33c are diagrams illustrating the process of multi-pass printing on output media.
Figure 33B:
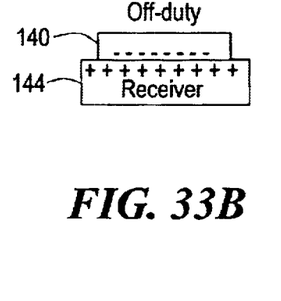
Figure 33C:
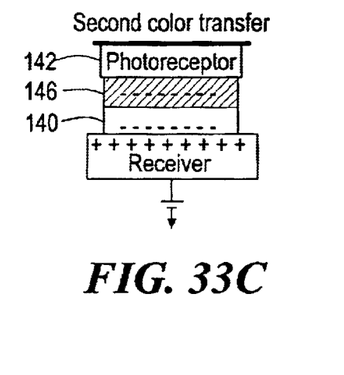
Figure 34:
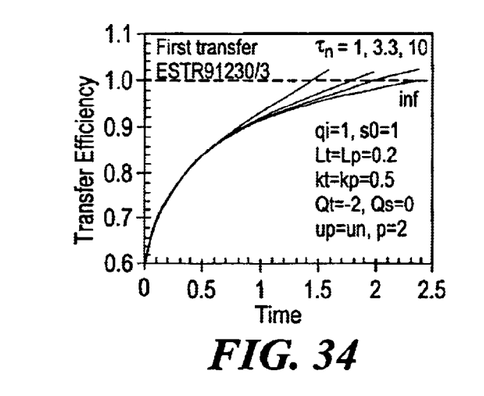
FIGS. 34–35 illustrates the transfer efficiency differences between passes in multi-pass reproduction.
Figure 35:
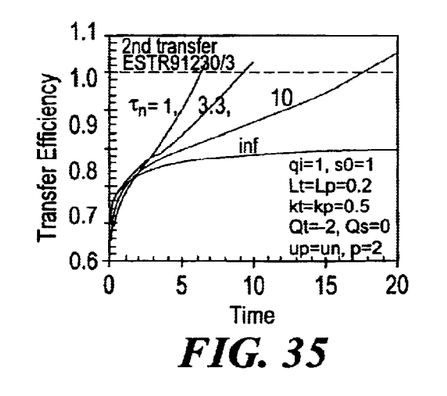

In color printing the failure to neutralize charge in toner from a first pass in a multi-pass color printing process will affect the transfer efficiency of the subsequent pass. As Shown in FIGS. 33a, b, c the residual charge in toner 140 applied from a photo receptor 142 to receiving media 144 impacts the application of a second toner layer 146 applied subsequently. Additional layers of toner may be placed down subsequently. Neutralization of the charge in an off duty or wait state as shown in FIG. 33b will allow the second color to faithfully be transferred depending on the amount of neutralization. This as a function of the time, tn, allowed for it to occur. The efficiency of this is shown in FIGS. 34 and 35 for first and second passes showing a marked efficiency reduction in later passes. This test allows selection of material for color printing to optimize quality and speed.

The test procedures noted above produce output values in the form of one or more parameters of dielectric relaxation of the materials under test. These materials typically are formed with a two dimensional surface and may be in thin sheets, on rollers, belts, drums or otherwise.

Figure 31A:
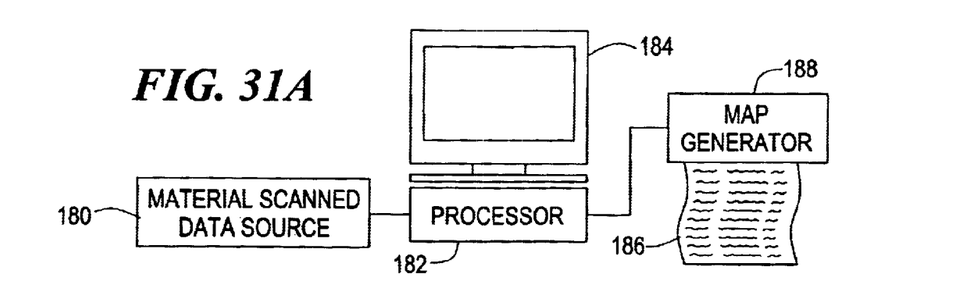
FIGS. 31a and 31b are system diagrams illustrating the creation of two dimensional output displays from data taken over an area of a material according to the invention.

The invention is also useful in the generation of two dimensional maps of the parameters of dielectric relaxation described above for material under test. This can be of value as documentary records for quality control, production analysis, aging information, and the like, applicable to output media, rollers, drums and belts among others. FIG. 31a illustrates an example of mapping of the dielectric relaxation data obtained by any of the scanning procedures and apparatus above described. An exemplary scanning system 180 provides output signals representative of one or more parameters of dielectric relaxation generated in these testing apparatus and provides it to a processor 182. Processor 182 performs the calculations described necessary to convert the raw data into actual parameters and format them for display on monitor 184 and also for output as a map 186 by printer 188. Such a map typically shows by color change, gray scale or otherwise the parameter as a function of position in the two dimensional material being tested. A map can be generated for each or either surface where surface properties are involved. The above identified U.S. Pat. No. 5,929,640 shows further details of such mapping techniques.

Figure 31B:
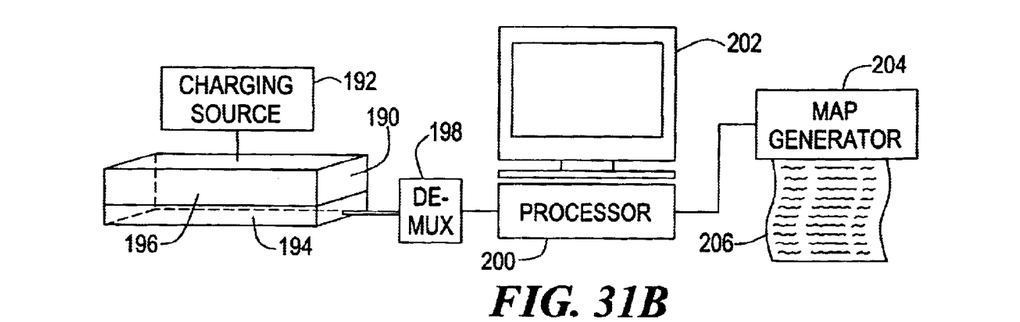
Figure 32:
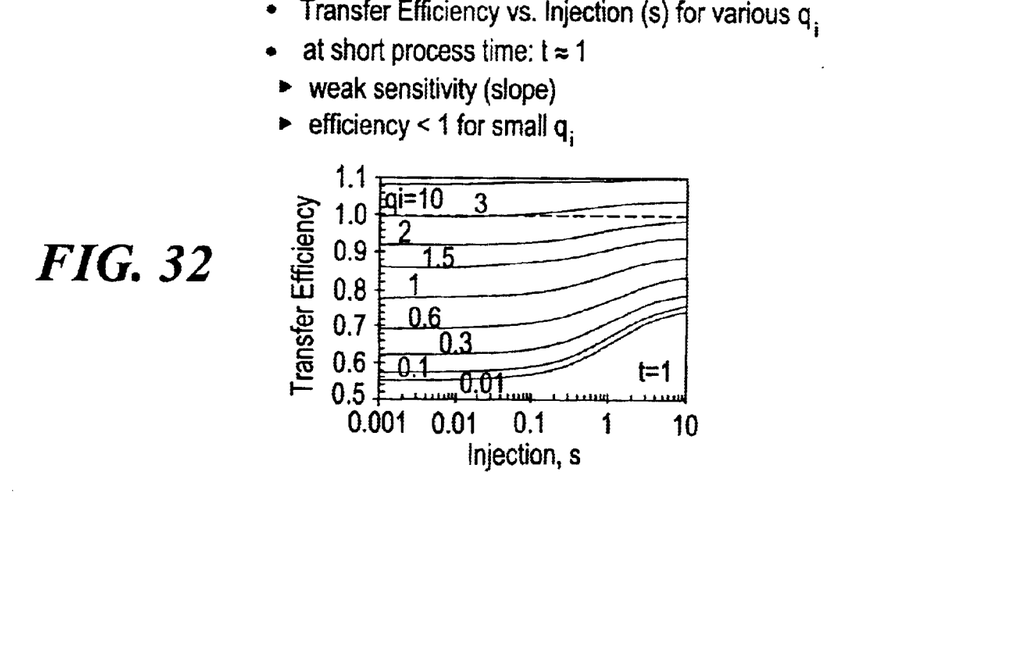
FIG. 32 is a graph illustrating the effect of parameters on duplex printing according to the invention.

Mapping or charting can also be applied to current flow of a non scanning test as shown in FIG. 31b. As shown there, a material 190 to be tested has charge applied to it through a source 192. Current flows out of the material through a matrix of conductors 194. The matrix includes an array of individual current sensors 196 for electronic scanning. Alternatively, the source is moved in two directions over the material sample for mechanically scanning. Both approaches provide current sensing over a two dimensional area of the material 190. The sensed current levels are applied through a demultiplexer 198 as appropriate to a processor 200 which performs required calculations to obtain the dielectric relaxation or response parameters desired from the set described above and formats them for display in a monitor 202. The processor 200 also formats the data for printing as a map or chart 206 by a printer 204. The Map 206 provides a two dimensional presentation of the parameters using techniques and for purposes described above.

While the description above focuses upon the application of the invention to electrophotographic printing, it may be used in any application where dielectric relaxation properties of materials affects their performance when exposed to electric fields or potentials.

What is claimed is:

1. Media for receiving electrophotographically generated images comprising;

image receiving material in the form of a two dimensional layer;

said material being selected for use in electrophotographic reproduction based on dielectric relaxation characteristics of said material;

said characteristics selected from the group including intrinsic charge density, charge mobility, surface charge injection, and dielectric constant.

2. The media of claim 1 wherein said intrinsic charge density is at least approximately 1.0 normalized unit, given by $\epsilon V m x^2/L^3$.

3. The media of claim 1 wherein said surface charge injection, in combination with an electrode placed in proximity to said layer, is at least approximately 0.1 normalized units, given by $\epsilon \mu V m x^2/L^3$.

* * * * *

UNITED STATES PATENT AND TRADEMARK OFFICE
CERTIFICATE OF CORRECTION

PATENT NO. : 6,670,814 B2
DATED : December 30, 2003
INVENTOR(S) : Tse

It is certified that error appears in the above-identified patent and that said Letters Patent is hereby corrected as shown below:

Column 10,
Line 6, "$\epsilon Vmx^2/L^3$" should read -- $\epsilon V_{mx}/L^2$ --; and
Line 10, "$\epsilon\mu Vmx^2/L^3$" should read -- $\epsilon\mu V_{mx}^2/L^3$ --.

Signed and Sealed this

Thirteenth Day of December, 2005

JON W. DUDAS
*Director of the United States Patent and Trademark Office*